(12) United States Patent
Kuo et al.

(10) Patent No.: US 10,987,173 B2
(45) Date of Patent: Apr. 27, 2021

(54) METHOD, SYSTEM AND APPARATUS FOR MAINTAINING PATIENT REGISTRATION IN A SURGICAL NAVIGATION SYSTEM

(71) Applicant: SYNAPTIVE MEDICAL (BARBADOS) INC., Bridgetown (BB)

(72) Inventors: Yu-Ching Audrey Kuo, Toronto (CA); Kirusha Srimohanarajah, Toronto (CA); Gal Sela, Toronto (CA); Alexander Gyles Panther, Toronto (CA); Kelly Noel Dyer, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 527 days.

(21) Appl. No.: 15/899,753

(22) Filed: Feb. 20, 2018

(65) Prior Publication Data

US 2018/0235714 A1 Aug. 23, 2018

(51) Int. Cl.
*A61B 34/20* (2016.01)
*G01R 33/28* (2006.01)
(Continued)

(52) U.S. Cl.
CPC ............ *A61B 34/20* (2016.02); *A61B 5/0037* (2013.01); *A61B 5/0064* (2013.01); *A61B 5/055* (2013.01);
(Continued)

(58) Field of Classification Search
CPC ............ A61B 90/39; A61B 2090/3954; A61B 2090/3937; A61B 2090/3983; A61B 2034/2055; A61B 5/055
See application file for complete search history.

(56) References Cited

U.S. PATENT DOCUMENTS

2004/0127788 A1* 7/2004 Arata ..................... A61B 6/032
600/424
2006/0050942 A1* 3/2006 Bertram ................. A61B 34/20
382/128

(Continued)

OTHER PUBLICATIONS

"An MRI Compatible Surface Scanner" by O.V. Olesen et al. Poster session presented at ISMRM Scientific Workshop, Tromso, Norway (Year: 2015).*

(Continued)

*Primary Examiner* — Jason M Ip
(74) *Attorney, Agent, or Firm* — Perry + Currier

(57) ABSTRACT

A method of maintaining patient registration in surgical navigation includes: obtaining a patient position in a tracking system frame of reference, based on a fiducial marker array affixed in a first position relative to the patient; receiving an initial surface scan depicting the patient and the fiducial array; responsive to receiving an intraoperative image depicting the patient: obtaining a position, in the tracking system frame of reference, of the fiducial array affixed in a second position relative to the patient; receiving a secondary surface scan depicting the patient and the fiducial array; detecting a deviation in a position of the fiducial marker array relative to the patient between the initial and secondary surface scans; and applying the deviation to the position of the patient to generate an updated position of the patient in the tracking system frame of reference, based on the fiducial array affixed in the second position.

13 Claims, 10 Drawing Sheets

(51) Int. Cl.
*A61B 5/055* (2006.01)
*A61B 5/11* (2006.01)
*A61B 90/00* (2016.01)
*A61B 5/00* (2006.01)

(52) U.S. Cl.
CPC .......... *A61B 5/0555* (2013.01); *A61B 5/1114* (2013.01); *A61B 5/706* (2013.01); *A61B 90/39* (2016.02); *G01R 33/283* (2013.01); *A61B 2034/2051* (2016.02); *A61B 2034/2065* (2016.02); *A61B 2090/363* (2016.02); *A61B 2090/364* (2016.02); *A61B 2090/3954* (2016.02)

(56) References Cited

U.S. PATENT DOCUMENTS

2014/0055133 A1* 2/2014 I .......................... A61B 5/055
  324/309
2015/0031985 A1 1/2015 Reddy et al.

OTHER PUBLICATIONS

CIPO, Examination Report, dated Jul. 26, 2017, re Canadian Patent Application No. 2958624.

* cited by examiner

METHOD, SYSTEM AND APPARATUS FOR MAINTAINING PATIENT REGISTRATION IN A SURGICAL NAVIGATION SYSTEM

FIELD

The specification relates generally to medical imaging, and specifically to a method, system and apparatus for maintaining patient registration in a medical imaging system.

BACKGROUND

Navigation systems are employed in various surgical contexts, permitting surgical tools to be tracked during a procedure and displayed alongside both preoperative and intraoperative patient images, surgical planning data, and the like.

Such systems generally require that a patient's position be registered with a tracking system, permitting the patient to be depicted alongside tracked surgical tools, for example. Registration may be accomplished, for example, by affixing fiducial markers in a known position relative to the patient. However, the markers may need to be removed—for example, when repositioning the patient to obtain an intraoperative (e.g. magnetic resonance imaging, MRI) image of the patient, as well as when repositioning the patient for further surgical intervention after the intraoperative image is captured. Removal of the fiducial markers results in loss of patient registration, which can reduce the accuracy of intraoperative image capture, and may necessitate a time-consuming repetition of the patient registration process after the intraoperative image is captured.

Additionally, positioning the patient within an imaging device such as an MRI scanner typically requires manual verification and adjustment of imaging configuration to account for the patient's orientation within the imaging device. Such verification and adjustment can be time-consuming procedures.

SUMMARY

According to an aspect of the specification, a method of maintaining patient registration in a surgical navigation system, comprising: obtaining, at a computing device of the medical imaging system, a position of a patient in a tracking system frame of reference, based on a fiducial marker array affixed in a first position relative to the patient; receiving, at the computing device, an initial surface scan depicting the patient and the fiducial marker array in the first position; responsive to receiving, from a medical imaging device, an intraoperative image depicting the patient: obtaining a position, in the tracking system frame of reference, of the fiducial marker array affixed in a second position relative to the patient; receiving a secondary surface scan depicting the patient and the fiducial marker array in the second position; detecting a deviation in a position of the fiducial marker array relative to the patient between the initial and secondary surface scans; and applying the deviation to the position of the patient to generate an updated position of the patient in the tracking system frame of reference, based on the fiducial marker array affixed in the second position.

According to another aspect of the specification, a computing device for maintaining patient registration in a surgical navigation system; comprising: a communications interface configured to connect with a surface scanner and a medical imaging device; a processor interconnected with the communications interface, the processor configured to: obtain a position of a patient in a tracking system frame of reference, based on a fiducial marker array affixed in a first position relative to the patient; receive an initial surface scan from the surface scanner, depicting the patient and the fiducial marker array in the first position; responsive to receiving, from the medical imaging device, an intraoperative image depicting the patient; obtain a position, in the tracking system frame of reference, of the fiducial marker array affixed in a second position relative to the patient; receive a secondary surface scan depicting the patient and the fiducial marker array in the second position; detect a deviation in a position of the fiducial marker array relative to the patient between the initial and secondary surface scans; and apply the deviation to the position of the patient to generate an updated position of the patient in the tracking system frame of reference, based on the fiducial marker array affixed in the second position.

BRIEF DESCRIPTIONS OF THE DRAWINGS

Embodiments are described with reference to the following figures, in which.

DETAILED DESCRIPTION OF THE EMBODIMENTS

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

Unless defined otherwise, all technical and scientific terms used herein are intended to have the same meaning as commonly understood to one of ordinary skill in the art. Unless otherwise indicated, such as through context, as used herein, the following terms are intended to have the following meanings;

As used herein the term "intraoperative" refers to an action, process, method, event or step that occurs or is carried out during at least a portion of a medical procedure. The term "preoperative" as used herein refers to an action, process, method, event or step that occurs or is carried out before the medical procedure begins. The terms intraoperative and preoperative, as defined herein, are not limited to surgical procedures, and may refer to other types of medical procedures, such as diagnostic and therapeutic procedures.

Figure 1:
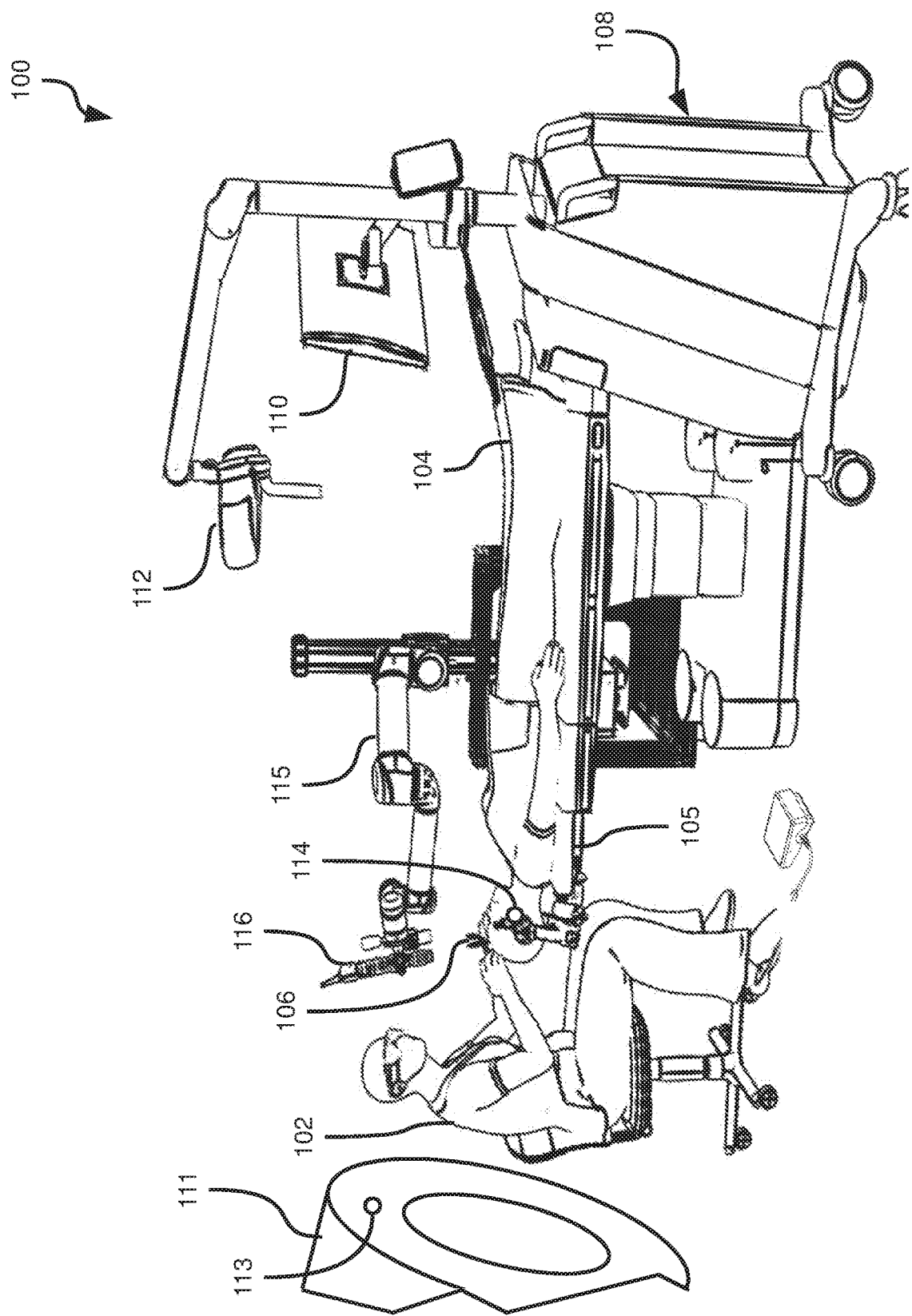
FIG. 1 depicts an operating theatre including a medical imaging system, according to a non-limiting embodiment.

FIG. 1 depicts a surgical operating theatre 100 in which a healthcare worker 102 (e.g. a surgeon) operates on a patient 104 lying on a bed 105. Specifically, surgeon 102 is shown conducting a minimally invasive surgical procedure on the brain of patient 104. Minimally invasive brain surgery involves the insertion and manipulation of instruments into the brain through an opening that is significantly smaller than the portions of skull removed to expose the brain in traditional brain surgery techniques. Surgical procedures other than brain surgery may also be performed in operating theatre 100 and make use of the systems and methods described herein.

The opening through which surgeon 102 inserts and manipulates instruments is provided by an access port 106. Access port 106 typically includes a hollow cylindrical device with open ends. During insertion of access port 106 into the brain (after a suitable opening has been drilled in the skull), an introducer (not shown) is generally inserted into access port 106. The introducer is typically a cylindrical device that slidably engages the internal surface of access port 106 and bears a conical atraumatic tip to allow for insertion of access port 106 into the brain. Following insertion of access port 106, the introducer may be removed, and access port 106 may then enable insertion and bimanual manipulation of surgical tools into the brain. Examples of such tools include suctioning devices, scissors, scalpels, cutting devices, imaging devices (e.g. ultrasound sensors) and the like.

Also shown in FIG. 1 is an equipment tower 108 supporting a computing device (not shown) such as a desktop computer, as well as one or more displays 110 connected to the computing device for displaying images provided by the computing device. The images provided to display 110 from the computing device can include images captured by a medical imaging device 111, which in the present embodiment is an MRI scanner (only partially visible in FIG. 1). A variety of other imaging devices are also contemplated, including, for example, computed tomography (CT) scanners and the like. Device 111 may be employed to capture images of patient 104 both before and during the medical procedure. To capture such images, patient 104 is repositioned (either by moving bed 105 or by placing patient 104 on another bed or gantry, not shown) into proximity with device 111 (for example, to place the head of patient 104 within the bore of the MRI scanner).

Equipment tower 108 also supports a tracking system 112. An example of tracking system 112 is the "Polaris" system available from Northern Digital Inc. Tracking system 112 is generally configured to track the positions of one or more fiducial markers mounted on any of the above-mentioned equipment. Tracking system 112 can include a camera (e.g. a stereo camera) and a computing device (either the same device as mentioned above or a separate device) configured to locate the fiducial markers in the images captured by the camera, and determine the spatial positions of the markers.

The nature of the markers and the camera are not particularly limited. For example, the camera may be sensitive to infrared (IR) light, and tracking system 112 may also include one or more IR emitters (e.g. IR light emitting diodes (LEDs)) to shine IR light on the markers. In other examples, marker recognition in tracking system 112 may be based on radio frequency (RF) radiation, visible light emitted from devices such as pulsed or un-pulsed LEDs, electromagnetic radiation other than IR or visible light, and the like. For RF and EM-based tracking, each object can be fitted with markers having signatures unique to that object, and tracking system 112 can include antennae rather than the above-mentioned camera. Combinations of the above may also be employed.

Each tracked object generally includes three or more markers fixed at predefined locations on the object. Example markers 113 and 114 are shown affixed to MRI scanner 111 and patient 104, respectively, although single markers are illustrated only for simplicity. In practice, each of MRI scanner 111 and patient 104 are provided with an array of markers. The predefined geometries of the marker arrays, and the locations of markers within the arrays are configured within tracking system 112. Thus, tracking system 112 is configured to capture images of operating theatre 100, and compare the positions of any visible markers to the pre-configured geometry and marker locations. Based on the comparison, tracking system 112 determines which marker arrays are present in the field of view of the camera, as well as what positions those objects are currently in.

Tracking system 112 therefore enables tracking of the position of patient 104 and MRI scanner 111 themselves, by detecting the location and position of marker arrays disposed at fixed positions relative to each of patient 104 and MRI scanner 111. The tracking of patient and imaging device positions will be described in greater detail further below.

Also shown in FIG. 1 is an automated articulated arm 115, also referred to as a robotic arm, carrying an external scope 116 (i.e. external to patient 104). External scope 116 may be positioned over access port 106 by robotic arm 115, and may capture images of the brain of patient 104 (or any other portion of patient 104, depending on the nature of the medical procedure being performed) for presentation on display 110. The movement of robotic arm 115 to place external scope 116 correctly over access port 106 may be guided by tracking system 112 and the computing device in equipment tower 108. The images from external scope 116 presented on display 110 may be overlaid with other images, including images obtained prior to the surgical procedure. The images presented on display 110 may also display virtual models of surgical instruments present in the field of view of tracking system 112 (the positions and orientations of the models having been determined by tracking system 112 from the positions of marker arrays, as mentioned above).

The medical procedure (e.g. the above-mentioned minimally invasive surgical procedure, such as a tumor resection) performed on patient 104 typically requires that patient 104 be on bed 105. Position tracking of patient 104 is enabled by affixing a marker array (illustrated as marker 114 in FIG. 1) directly to patient 104, to bed 105, or to an intermediate structure, such as a head holder fixing the skull of patient 104 to bed 105.

During the procedure, it may be necessary to acquire one or more intraoperative images of patient 104 using MRI scanner 111 (or any other suitable imaging device). Patient 104 must therefore be repositioned from bed 105 onto a gantry (not shown) associated with MRI scanner 111. Bed 105 itself may also be repositioned to place patient 104 within MRI scanner 111. Once patient 104 has been repositioned, instructions are provided (e.g. by the above-mentioned computing device) to MRI scanner 111 to capture one or more images of patient 104. Such instructions may be required to specify the position of patient 104 relative to MRI scanner 111, as will be discussed in greater detail below.

When the intraoperative image or images have been acquired, patient 104 is repositioned again, substantially returning to the position shown in FIG. 1, for continuation of the medical procedure. The repositioning of patient 104 presents challenges in maintaining the tracked position of patient 104, as will be discussed below.

Figure 2A:
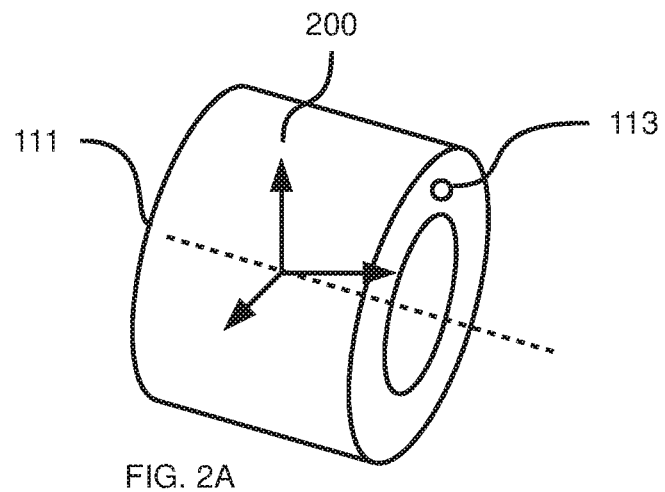
FIGS. 2A-2C depicts various frames of reference at use in the medical imaging system of FIG. 1, according to a non-limiting embodiment.
Figure 2B:
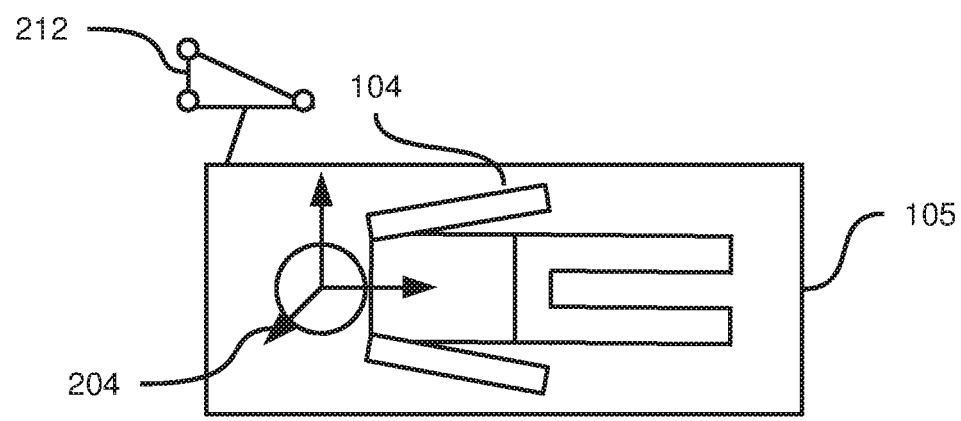
Figure 2C:
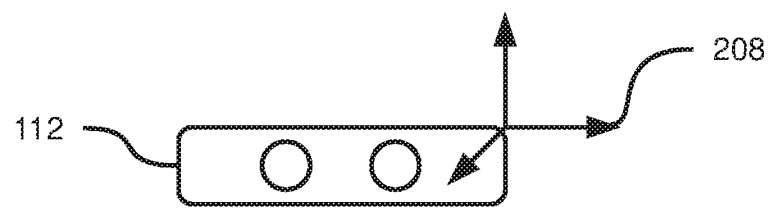

Turning to FIGS. 2A-2C, various frames of reference employed in operating theatre 100 are illustrated, MRI scanner 111, for example, employs a frame of reference 200 (FIG. 2A) that establishes a coordinate system having an origin at a known location within MRI scanner 111. Instructions to MRI scanner 111, such as instructions to capture an image, generally identify a target location within MRI scanner 111 in frame of reference 200. That is, an instruction to MRI scanner 111 may identify a location that is at a specified distance along each of three axes from the origin of frame of reference 200. The origin may be the isocentre of the magnet in MRI scanner 111, or any other predefined location within MRI scanner 111. The capture instructions may also identify the orientation of the patient in frame of reference 200, to configure the imaging parameters employed by MRI scanner 111 (e.g. if a patient is supine, different imaging parameters may be employed than if the patient is prone).

FIG. 2B illustrates a patient frame of reference 204, by which locations within patient 104 are identified. For example, if an image of a certain portion of patient 104 is desired, that portion is originally identified by a specified distance along each of three axes from an origin at a known location on patient 104. The origin may be at a predefined anatomical location, and the axes may be defined in a variety of ways. Conventionally, the axes are defined by the intersections of the sagittal, coronal and transverse planes. The axes may be referred to, for example, as the Left (intersection of coronal and transverse planes), Posterior (intersection of sagittal and transverse planes) and Superior (intersection of sagittal and coronal planes) axes (LPS).

FIG. 2C illustrates a tracking system frame of reference 208. Frame of reference 208 has an origin at a known location within operating theatre 100 (that is, within the field of view of the camera of tracking system 112, illustrated in FIG. 2C). Coordinates within frame of reference 208 thus define locations within operating theatre 100, independently of patient 104 and MRI scanner 111. Locations of marker-equipped tools are determined by tracking system 112 in frame of reference 208. In addition, to track the position of patient 104 tracking system 112 typically does not track patient 104 directly, but instead tracks a marker array, such as array 212 shown in FIG. 2B. Either tracking system 112 or the computing device mentioned above store a fixed relationship between the position of array 212 and the position of frame of reference 204. For example, the relationship may be stored as a vector from the current position of array 212 to the origin of frame of reference 204, along with orientations of the axes of frame of reference 204.

The above relationship is established by affixing array 212 relative to patient 104, and then employing a tracked pointer or other instrument to point to known locations on patient 104 (such as the origin of frame of reference 204). The vector defining the position of patient 104 relative to array 212 is stored in memory, and thereafter, by detecting array 212 tracking system can infer the position of patient 104. Similarly, the position of MRI scanner 111 can be determined by storing another vector defining the position of frame of reference 200 relative to marker 113 (or an array of markers, not shown).

During the above-mentioned repositioning of patient 104 to acquire intraoperative images, it is often necessary to remove array 212 (e.g. because array 212 does not fit within the bore of MRI scanner 111). Therefore, tracking system 112 is unable to track the position of patient 104 as patient 104 is repositioned within MRI scanner 111. Further, following image acquisition, array 212 is re-affixed to patient 104, bed 105 or the like. However, the position of array 212 is not likely to coincide exactly with the original position in connection with which patient registration was established. Therefore, the store vector defining the spatial relationship between frame of reference 204 and array 212 may be invalid.

As will be discussed below, the computing device in equipment tower 108 is configured to perform various actions that facilitate the maintenance or recovery of patient registration following the removal or replacement of array 212.

Figure 3:
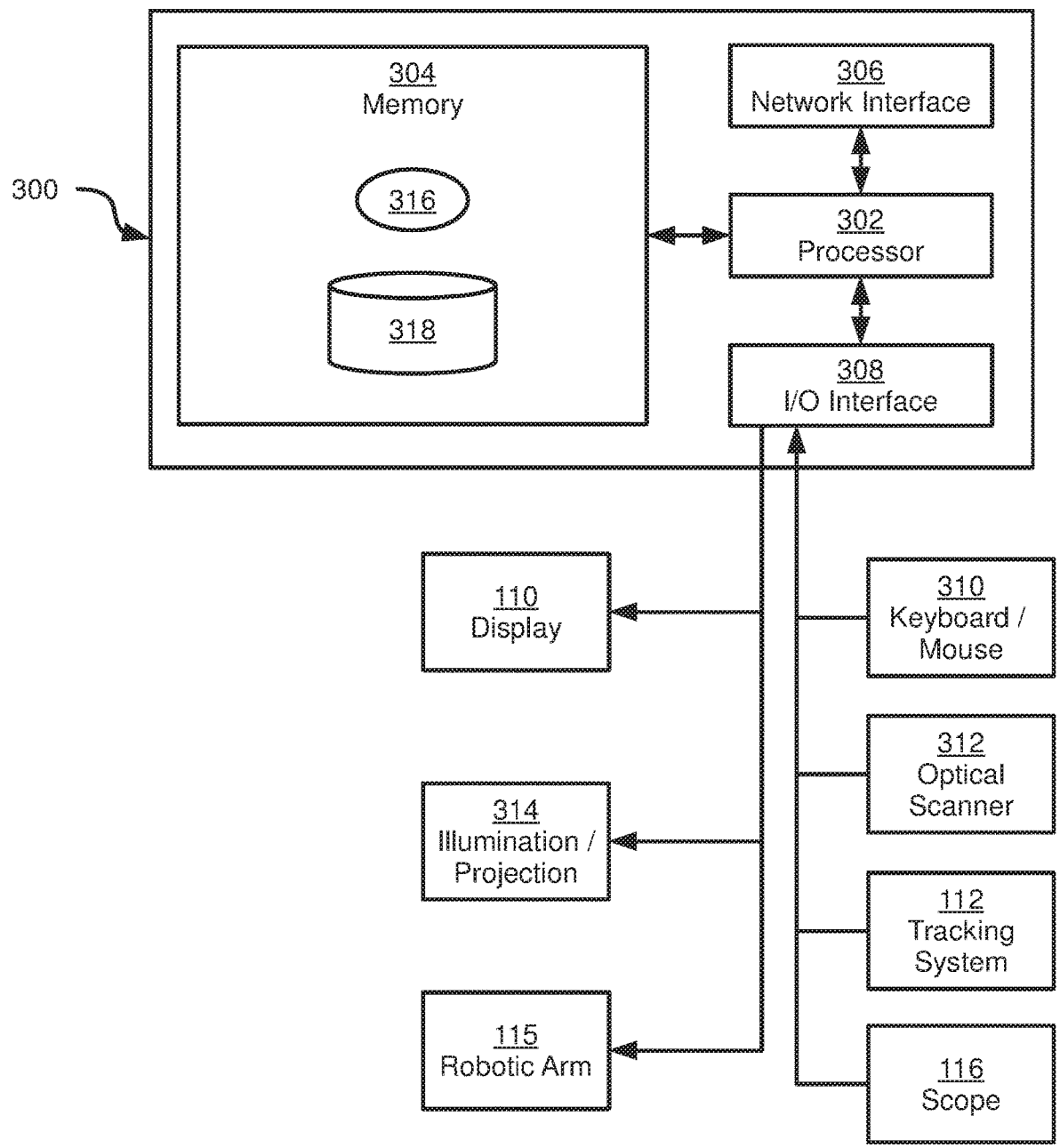
FIG. 3 depicts certain components of a computing device as implemented in the medical imaging system of FIG. 1, according to a non-limiting embodiment.

Before a discussion of the functionality of the computing device, a brief description of the components of the computing device will be provided. Referring to FIG. 3, a computing device 300 is depicted, including a central processing unit (CPU, also referred to as a microprocessor or simply a processor) 302 interconnected with a non-transitory computer readable storage medium such as a memory 304.

Processor 302 and memory 304 are generally comprised of one or more integrated circuits (ICs), and can have a variety of structures, as will now occur to those skilled in the art (for example, more than one CPU can be provided). Memory 304 can be any suitable combination of volatile (e.g. Random Access Memory ("RAM")) and non-volatile (e.g. read only memory ("ROM"), Electrically Erasable Programmable Read Only Memory ("EEPROM"), flash memory, magnetic computer storage device, or optical disc) memory. In the present example, memory 304 includes both a volatile memory and a non-volatile memory. Other types of non-transitory computer readable storage medium are also contemplated, such as compact discs (CD-ROM, CD-RW) and digital video discs (DVD).

Computing device 300 also includes a network interface 306 interconnected with processor 302. Network interface 306 allows computing device 300 to communicate with other computing devices via a network (e.g. a local area network (LAN), a wide area network (WAN) or any suitable combination thereof). Network interface 306 thus includes any necessary hardware for communicating over such networks, such as radios, network interface controllers (NICs) and the like.

Computing device 300 also includes an input/output interface 308, including the necessary hardware for interconnecting processor 302 with various input and output devices. Interface 308 can include, among other components, a Universal Serial Bus (USB) port, an audio port for sending and receiving audio data, a Video Graphics Array (VGA), Digital Visual Interface (DVI) or other port for sending and receiving display data, and any other suitable components.

Via interface 308, computing device 300 is connected to input devices including a keyboard and mouse 310, an optical scanner 312 (e.g. a laser-based depth scanner configured to generate point cloud data), as well as external scope 116 and tracking system 112, mentioned above. Also via interface 308, computing device 300 is connected to output devices including illumination or projection components 314 (e.g. lights, projectors and the like), as well as display 110 and robotic arm 115 mentioned above. Other input (e.g. touch screens) and output devices (e.g. speakers) will also occur to those skilled in the art.

It is contemplated that I/O interface 308 may be omitted entirely in some embodiments, or may be used to connect to only a subset of the devices mentioned above. The remaining devices, or all devices if I/O interface 308 is omitted, may be connected to computing device 300 via network interface 306.

Computing device 300 stores, in memory 304, a registration maintenance application 316 (also referred to herein as application 316) comprising a plurality of computer readable instructions executable by processor 302. When processor 302 executes the instructions of application 316 (or, indeed, any other application stored in memory 304), processor 302 performs various functions implemented by those instructions, as will be discussed below. Processor 302, or computing device 300 more generally, is therefore said to be "configured" or "operating" to perform those functions via the execution of application 316.

Also stored in memory 304 are various data repositories, including a patient data repository 318. Patient data repository 318 can contain a surgical plan defining the various steps of the minimally invasive surgical procedure to be conducted on patient 104, as well as image data relating to patient 104, such as images captured using MRI scanner 111. Repository 318 can also contain patient registration information, such as the above-mentioned vectors defining the spatial relationship between patient 104 and array 212.

As mentioned above, computing device 300 is configured, via the execution of application 316 by processor 302, to perform various actions related to facilitating the maintenance or recovery of patient registration. Those functions will be described in further detail below.

Figure 4:
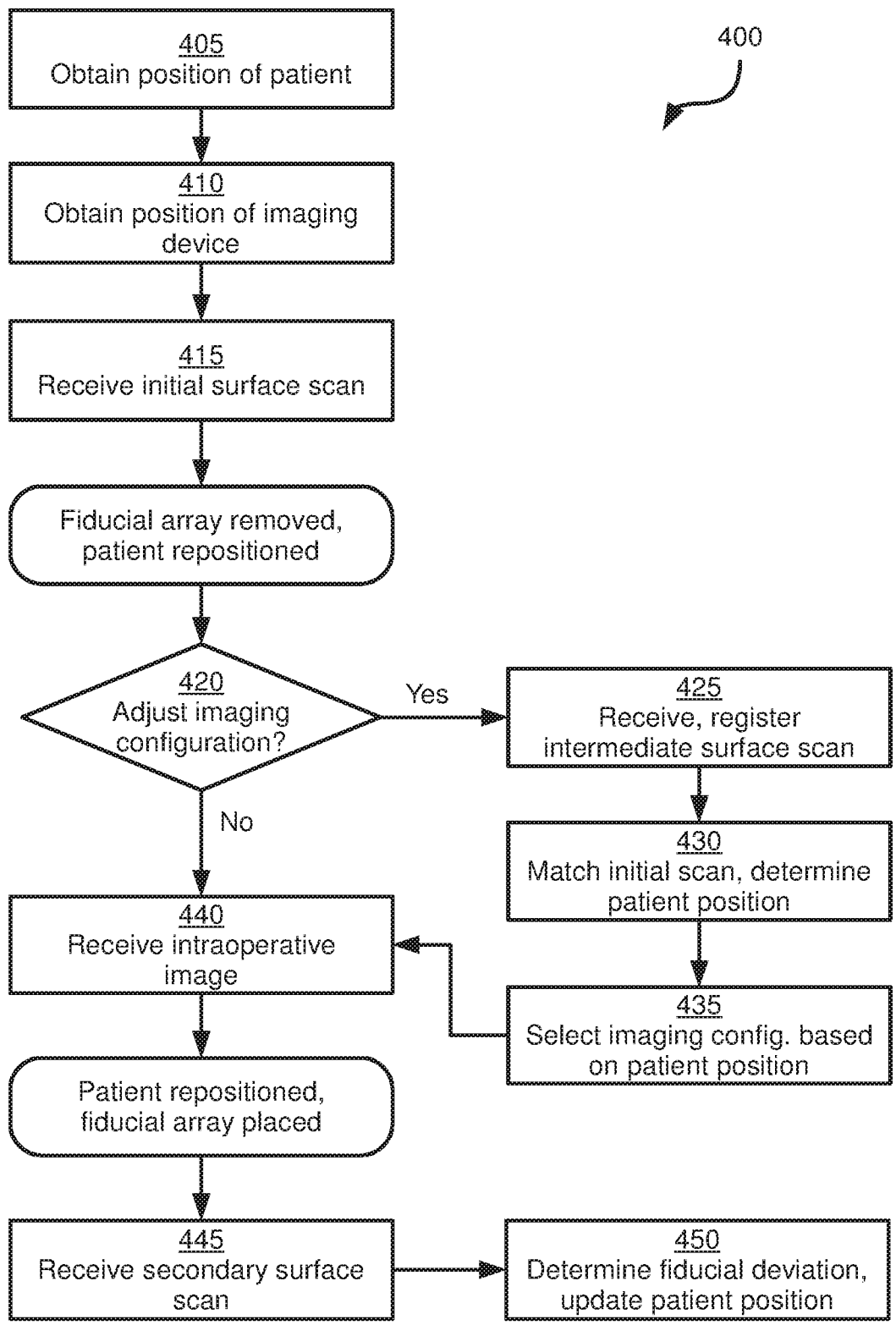
FIG. 4 depicts a method of transferring patient registration in the medical imaging system of FIG. 1, according to a non-limiting embodiment.

Referring now to FIG. 4, a method 400 of maintaining patient registration is depicted. Method 400 will be discussed in conjunction with its performance on computing device 300 as deployed in operating theatre 100. It will be apparent to those skilled in the art, however, that method 400 can also be implemented on other computing devices in other systems.

Beginning at block 405, computing device 300 is configured to obtain the position of patient 104. The position obtained at block 405 is obtained within frame of reference 208. That is, the location of patient 104 is obtained as coordinates within frame of reference 208, representing the location of the origin of patient frame of reference 204 (and, optionally, vectors indicating the orientations of the axes of frame of reference 204 within frame of reference 208). The position of patient 104 is obtained via the detection, by tracking system 112, of the location and orientation of marker array 212, and the application of stored patient registration vector data (mentioned earlier) to that location and orientation.

The position may be obtained by computing device 300 via receipt from tracking system 112, or the position may be obtained by computing device 300 by assisting tracking system 112 in the determination of the position. For instance, computing device 300 may receive raw image data from tracking system 112, identify array 212 within the raw data and apply the patient registration vector data.

At block 410, computing device 300 is configured to obtain the position of an imaging device such as MRI scanner 111. As in block 405, the position obtained at block 410 is obtained within frame of reference 208 (that is, the physical location of MRI scanner 111 within operating theatre 100). The position of MRI scanner 111 within operating theatre 100 may be obtained from tracking system 112. Tracking system 112, either independently or in conjunction with computing device 300, can be configured to detect marker 113 (and any other markers affixed to MRI scanner 111) and, based on the positions of such markers and a stored model of the geometry of MRI scanner 111 (or the geometry of a marker array affixed to MRI scanner 111 in combination with a registration vector), determine the position and orientation of MRI scanner 111 within operating theatre 100.

Blocks 405 and 410 can be performed substantially simultaneously. That is, tracking system 112 can capture an image that encompasses both array 212 and marker 113, and based on that image, determine both of the above-mentioned positions. The positions obtained at blocks 405 and 410 are stored in memory 304.

Figure 5:
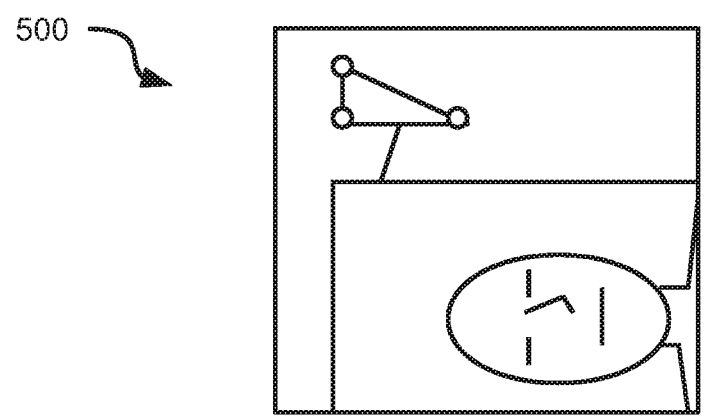
FIG. 5 depicts an initial surface scan received by the computing device of the system of FIG. 1 during the performance of the method of FIG. 4.

At block 415, computing device 300 is configured to receive, for example via interface 308, an initial surface scan depicting patient 104 and array 212 in a first position—that is, in the position in which array 212 appeared at block 405. For example, the surface scan may depict patient 104 and array 212 as shown in FIG. 2B. The nature of the surface scan is not particularly limited. In the present embodiment, the surface scan is received as point cloud data from optical scanner 312, which is a handheld optical scanner. For example, optical scanner 312 may include one or more laser emitters and one or more light sensors for measuring the depth (relative to the scanner itself) of a plurality of points in the field of view of the scanner. The point cloud data received at block 415 therefore includes, for each of a plurality of points (some representing at least a portion of patient 104, and some representing array 212), a three-dimensional position in a scan frame of reference distinct from any of the frames of reference discussed in connection with FIGS. 2A-2C. Referring to FIG. 5, an example initial surface scan 500 is illustrated, although it will be understood that the point cloud data received from scanner 312 need not be graphical data, but is rather illustrated as such in FIG. 5.

In some embodiments, the performance of block 415 can include the registration of the surface scan data to the tracking system frame of reference. For example, computing device 300 can be configured to detect the points in the surface scan corresponding to array 212. Since the position of array 212 in tracking system frame of reference 208 is known, computing device 300 can register the detected points to frame of reference 208. Further, since the point cloud data itself indicates the position of each point relative to other points, once the points depicting array 212 have been registered, the remaining points can also be registered, for example by assigning each point in the surface scan a set of coordinates in frame of reference 208.

Figure 6:
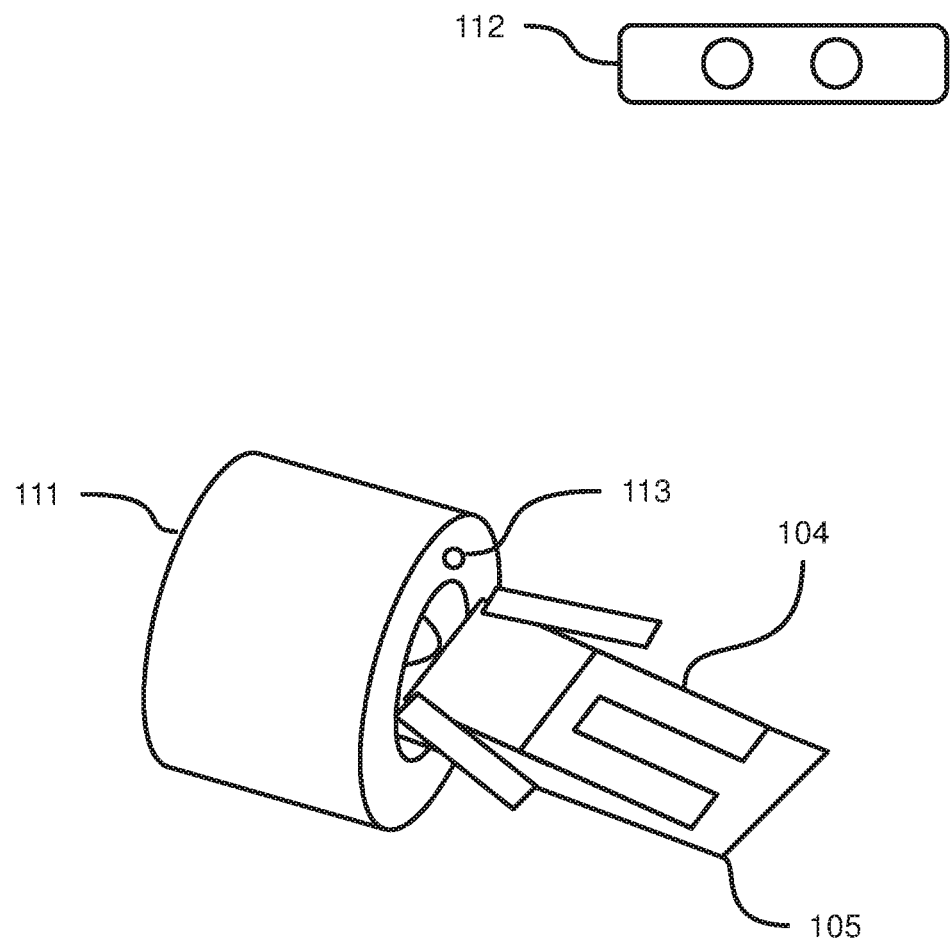
FIG. 6 depicts the patient and medical imaging device of the system of FIG. 1, arranged to capture an intraoperative image, according to a non-limiting embodiment.

Following the receipt of the initial surface scan, and typically following a portion of the medical procedure, patient 104 is repositioned for acquisition of an intraoperative image. In the present example, patient 104 is repositioned from the position shown in FIG. 1 to a position shown in FIG. 6, with the head of patient 104 place within the bore of MRI scanner 111. As will now be apparent from a comparison of FIG. 2B and FIG. 5, the bore of MRI scanner 111 provides insufficient space to accommodate array 212, and array 212 has therefore been removed. As a result, the camera of tracking system 112 can no longer track the position of array 212, and computing device 300 can therefore no longer obtain the position of patient 104.

Following the repositioning of patient 104, computing device 300 is configured to determine whether to adjust the imaging configuration for MRI scanner 111. The determination at block 420 can be made by the receipt of input data from an operator of computing device 300, indicating whether or not adjustment is required. In other embodiments, computing device 300 can be configured to omit the determination at block 420, and either always perform the tasks illustrated in FIG. 4 as following a "yes" determination, or always perform the tasks illustrated as following a "no" determination.

MRI scanner 111 employs magnetic gradients intended to align with various axes of patient 104. That is, a default configuration of MRI scanner 111 assumes a certain relationship between frame of reference 200 and frame of reference 204. For example, the default configuration may assume that the superior axis of frame of reference 204 is parallel to the axis of the bore of MRI scanner 111. Minor deviations in patient position (e.g., a deviation of below ten degrees between the patient superior axis and the bore axis) may have little or no effect on the resulting image acquired by MRI scanner 111. However, greater deviations may negatively impact the fidelity of images acquired by MRI scanner 111. Therefore, it may be advantageous to adjust the orientation of the above-mentioned gradients based on the position of patient 104 in MRI scanner 111, by making an affirmative determination at block 420.

Following an affirmative determination at block 420, computing device 300 proceeds to block 425. At block 425, computing device 300 is configured to receive an intermediate surface scan. As with the initial surface scan, the intermediate surface scan defines point cloud data; however, the intermediate scan depicts a portion of patient 104 (at least partially overlapping with the portion depicted in the initial scan) as positioned within MRI scanner 111, and does not depict array 212. The intermediate surface scan, in the present embodiment, is received from an optical scanner mounted within the bore of MRI scanner 111. The optical scanner may be scanner 312—that is, MRI scanner 111 may include a mounting structure for accepting scanner 312 in a fixed, known position within the bore—or the optical scanner may be a different scanner than the device from which the initial scan data was received.

Figure 7A:
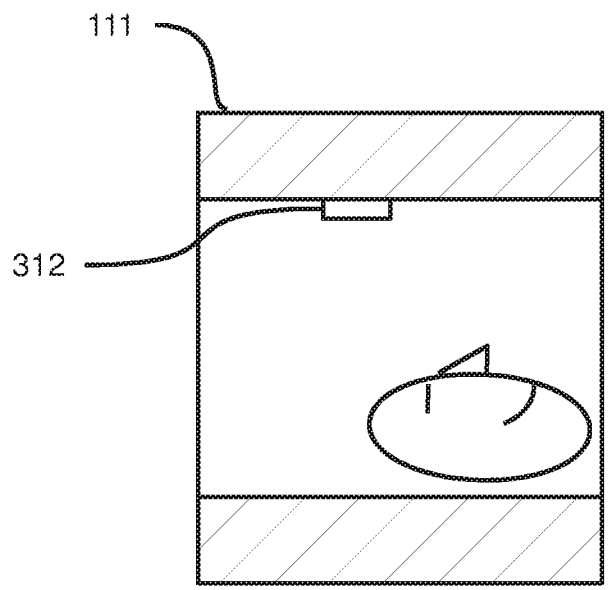
FIG. 7A depicts the patient of FIG. 1 repositioned for acquisition of an intraoperative image, according to a non-limiting embodiment.
Figure 7B:
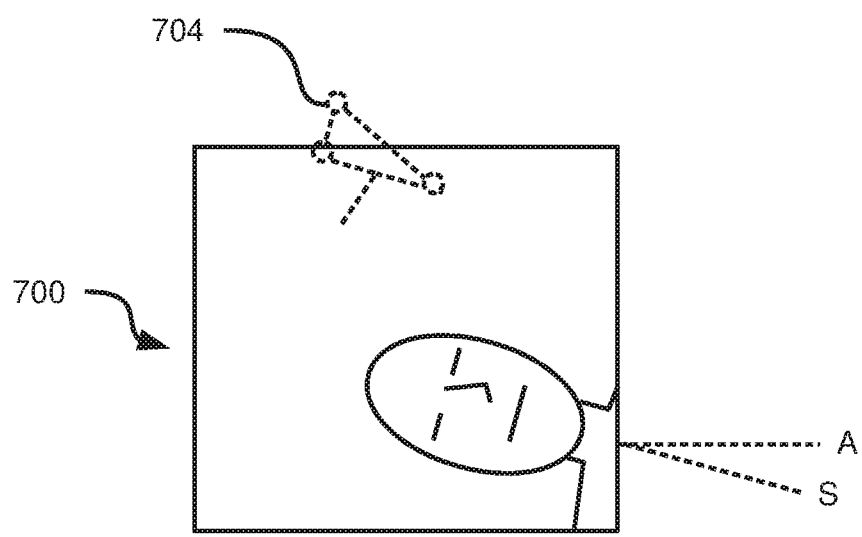
FIG. 7B depicts an intermediate surface scan acquired in the position shown in FIG. 7A, according to a non-limiting embodiment.

FIG. 7A depicts patient 104 within the bore of MRI scanner 111, as well as optical scanner 312 mounted within the bore of MRI scanner 111. FIG. 7B depicts an intermediate surface scan 700, acquired by scanner 312 in the position shown in FIG. 7A. Returning to FIG. 4, at block 425 the intermediate surface scan is also registered to tracking system frame of reference 208. Registration of scan 700 to frame of reference 208 is accomplished by use of the position of MRI scanner 111 obtained at block 410, along with the known position of optical scanner 312 relative to MRI scanner 111.

The position of patient 104 cannot be directly derived from scan 700, even once scan 700 has been registered in frame of reference 208. Instead, at block 430, computing device 300 is configured to register intermediate scan 700 and initial scan 500 to a common frame of reference (e.g. the frame of reference of scan 700), and based on that registration determine a virtual position for array 212. That is, computing device 300 is configured to match the depictions of patient 104 in scans 500 and 700 (by any suitable known image registration technique), and based on the position of array 212 in scan 500, to determine where array 212 would appear in scan 700 if array 212 were present in the field of view of scanner 312. Returning to FIG. 7B, a virtual depiction 704 of array 212 is shown, indicating where in scan 700 array 212 would be depicted, if array 212 had been present.

Because scan 700 is registered to frame of reference 208, once the virtual position of array 212 within scan 700 is established, the virtual position of array 212 in frame of reference 208 can be determined. As a result, by applying the previously mentioned patient registration vector data, computing device 300 can conclude the performance of block 430 by determining the position of patient 104 in frame of reference 208, despite the physical absence of array 212.

At block 435, having determined the position of patient 104, and having previously obtained the position of MRI scanner 111, computing device 300 is configured to automatically select an imaging configuration for MRI scanner 111 based on a comparison of the position of patient 104 and the position of MRI scanner 111. For example, computing device 300 can be configured to determine a deviation between the actual position of patient 104 (i.e, of frame of reference 204) and the default, or expected, position of patient 104 for MRI scanner 111. Referring to FIG. 7B, it is evident that the superior axis S of patient 104 is disposed at an angle of about fifteen degrees relative to the axis A of the bore of MRI scanner 111. The deviation may include any combination of rotations and translations, and can be determined based on any suitable conventional algorithm. The imaging configuration selected at block 435 can also include an imaging volume (i.e, the size of the space to be imaged).

The default gradients for MRI scanner 111 may be configured assuming that axis S is parallel with axis A. Therefore, at block 435 computing device 300 may select an imaging configuration that modifies the gradients to accommodate the actual orientation of patient 104. The selection can include a computation of gradient alignments (e.g. in frame of reference 200), or the selection can include simply communicating the above-mentioned deviation to MRI scanner 111, which itself can be configured to select the appropriate modified gradients.

Returning to FIG. 4, having selected an imaging configuration at block 435, computing device 300 is configured to continue the performance of method 400 at block 440. Alternatively, if the determination at block 420 is negative, the performance of blocks 425-435 is omitted, and computing device proceeds directly to block 440, without modifying the default imaging configuration for MRI scanner 111.

At block 440, computing device 300 is configured to receive an intraoperative image of patient 104 from MRI scanner 111. The intraoperative image can be received via interface 308 or network interface 306, and can be stored in repository 318. In some embodiments, computing device 300 itself is configured to control MRI scanner 111 to acquire the intraoperative image. In other embodiments, however, MRI scanner 111 may be controlled directly by an operator, or by a distinct computing device, and computing device 300 may simply receive the resulting image(s).

Following acquisition of the intraoperative image, patient 104 is removed from MRI scanner 111 and returned to substantially the position shown in FIG. 1, for continuation of the medical procedure. Array 212 is also replaced, however as will be apparent to those skilled in the art, the location of array 212 may not be identical to its original location as shown in FIG. 2B. In other words, the patient registration vector data defining the position of frame of reference 204 relative to the tracked position of array 212 in frame of reference 208 may no longer be accurate.

In order to reduce or eliminate the need to repeat a time-consuming manual patient registration process, computing device 300 is configured, at block 445, to receive a secondary surface scan (e.g. from a handheld optical scanner, such as scanner 312, having been removed from MRI scanner 111). The secondary scan depicts at least a portion of patient 104 (at least partially overlapping with the portion depicted in the initial surface scan), as well as array 212 in a second position.

Figure 8A:
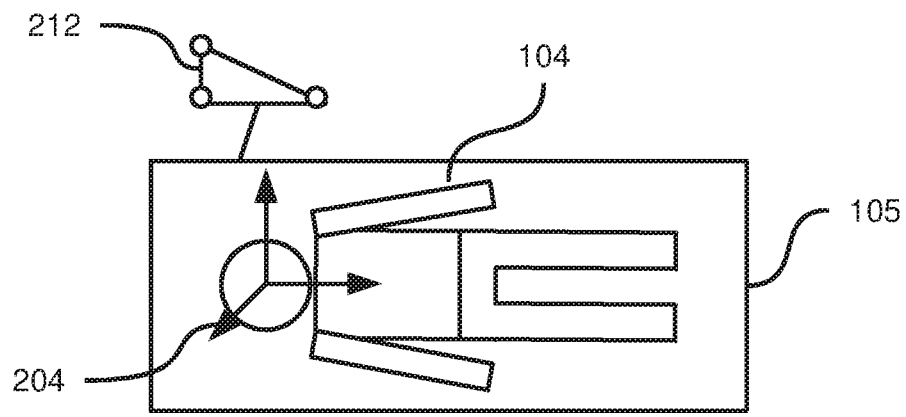
FIG. 8A depicts the patient of FIG. 1, repositioned for continuation of a medical procedure, following acquisition of an intraoperative image, according to a non-limiting embodiment.
Figure 8B:
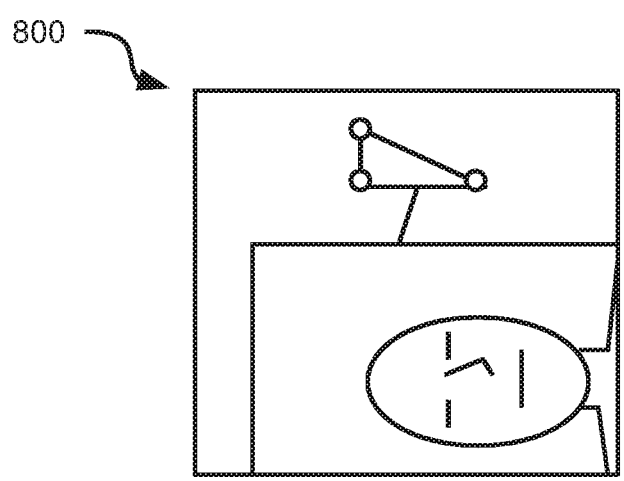
FIG. 8B depicts a secondary surface scan acquired in the position shown in FIG. 8B, according to a non-limiting embodiment.

Referring to FIG. 8A, patient 104 is depicted with array 212 reaffixed to bed 105, in a different position than that shown in FIG. 2B. FIG. 8B illustrates a secondary scan 800, depicting the head of patient 104 on bed 105, as well as array 212 in its second position (further from the head of bed 105 than the first position of array 212).

At block 450, having received the secondary surface scan, computing device 300 is configured to detect a deviation in the position of array 212 relative to patient 104 between the initial and secondary surface scans 500 and 800. More specifically, computing device 300 is configured to register scans 500 and 800 to a common frame of reference based on the point cloud data depicting patient 104, to identify the remainder of the point cloud data depicting array 212 in each scan, and determine a deviation (e.g. translation, rotation, scaling, and the like) between the depiction of array 212 in scan 500, and the depiction of array 212 in scan 800.

Figure 9:
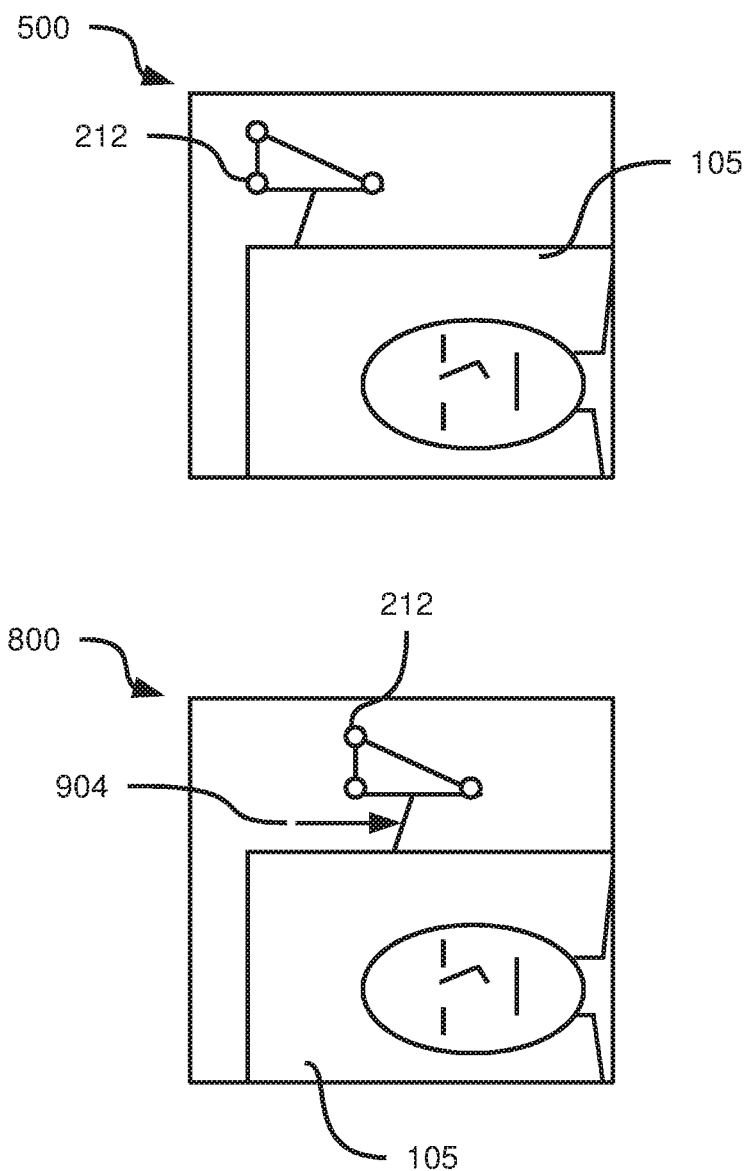
FIG. 9 depicts a deviation in the position of a marker array affixed to the patient of FIG. 1.

Referring to FIG. 9, scans 500 and 800 are shown, and a deviation 904 is illustrated, in the form of a translation indicating that array 212, in the second position, is a certain distance further from the head of bed 105 than in the first position. Following determination of the deviation, computing device 300 is configured to apply the deviation to the patient registration vector previously stored in memory 304, to generate an updated patient registration vector, from which an updated patient position can be obtained based on the position of array 212 in frame of reference 208. In such a manner, patient registration is maintained without the need to repeat a manual registration process to generate a new registration vector.

In other embodiments, computing device 300 can perform block 450 without registering scans 500 and 800 to a common frame of reference. In such embodiments, computing device 300 is configured to detect a predetermined set of anatomical features of patient 104 in each of scans 500 and 800. For example, computing device 300 can store in memory 304 image attributes permitting computing device 300 to detect the ears, eyes and nose of patient 104. Computing device 300 is configured to detect such features in each of scans 500 and 800, and to determine vectors between array 212 and those features in each of the scans. In other words, computing device 300 determines a depicted position of array 212 relative to the anatomical features in each scan. By comparing the depicted positions from scans 500 and 800, computing device 300 is then configured to determine the above-mentioned deviation.

Variations to the above systems and methods are contemplated. For example, although the surface scans mentioned above depict patient 104, the scans may also depict other equipment affixed to patient 104. For example, in brain surgery, the head of patient 104 is typically affixed to a head holder (not shown) to reduce or eliminate movement of the head during the procedure. The head holder is generally not removed until the procedure is complete, and therefore appears in surface scans. The features of the head holder may also be employed in registering the surface scans to each other.

In some embodiments, blocks 425-435 may be replaced with the capture of a scout intraoperative image, which may be compared to an atlas image or a preoperative image of patient 104 depicting the expected (or default) patient position within MRI scanner 111. From that comparison, the deviation between the actual patient position and the expected patient position may be determined, and an imaging configuration may be selected for further intraoperative images.

In further embodiments, imaging configuration adjustment at blocks 425-435 can be achieved without reference to the initial surface scan at block 415. For example, when optical scanner 312 is mounted at a known position within imaging device 111 as shown in FIG. 7A, the position of scanner 312 (and therefore of any point cloud data generated by scanner 312) relative to frame of reference 200 is known. At block 425, a surface scan is captured by scanner 312 and registered to frame of reference 200 by virtue of the known fixed transformation between scanner 312 and frame of reference 200. Rather than comparing the scan from block 425 to a previous scan, the scan from block 425 can instead be compared to an atlas image having an anatomical alignment corresponding to the default configuration for device 111.

Based on the comparison, computing device 300 is configured to determine a transformation between the surface scan and the atlas; the transformation indicates the actual position of the patient relative to "expected" default patient position corresponding to the default imaging configuration of device 111. That transformation can then be employed to select an updated imaging configuration at block 435, as described above. In the above embodiment, if regaining patient registration with a tracking system is not required (e.g. when the image obtained at block 440 is a diagnostic image rather than an intraoperative image), blocks 405-415 and blocks 445-450 can be omitted.

Figure 10:
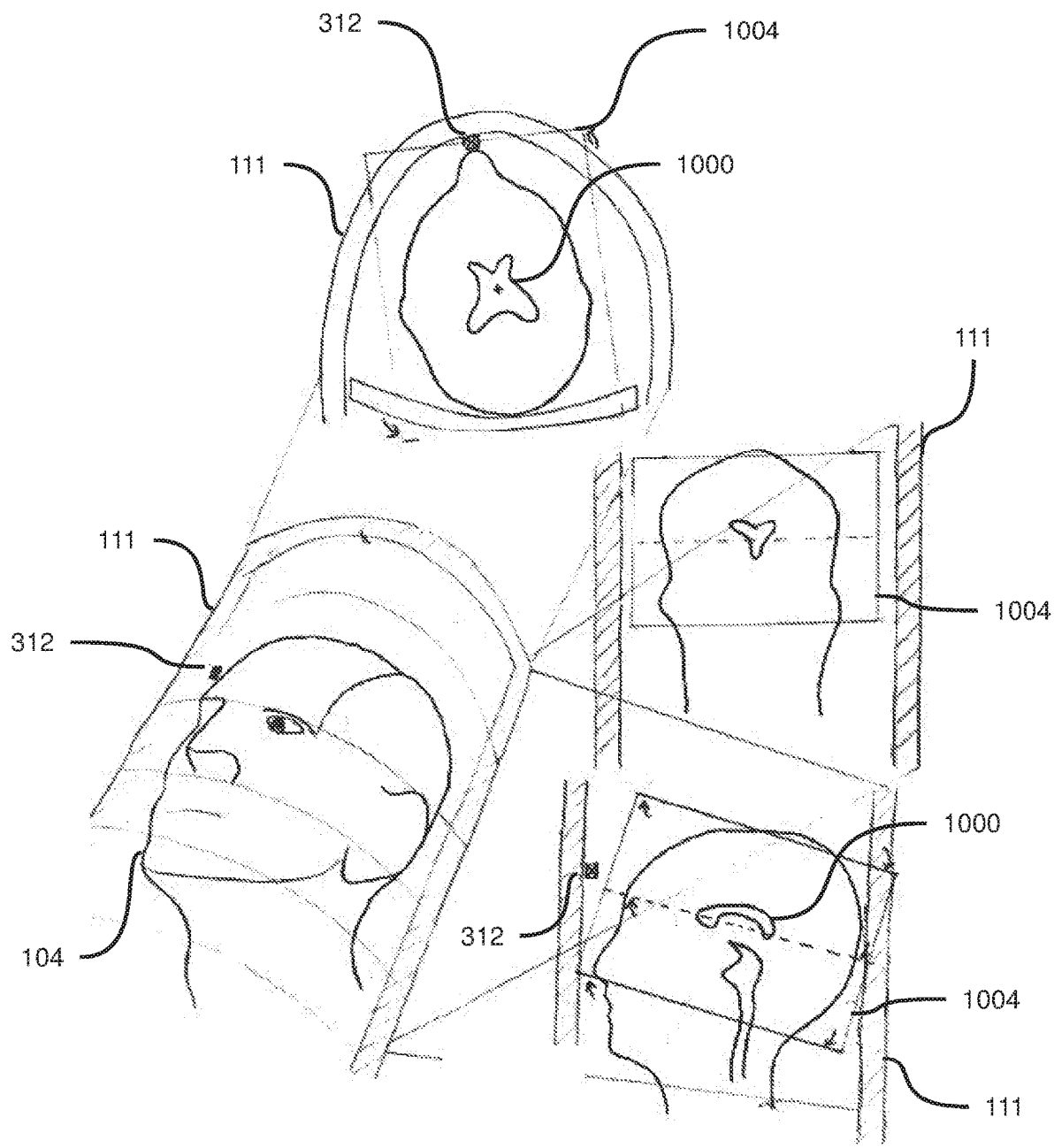
FIG. 10 depicts the generation of an adjusted imaging volume based on a surface scan of the patient of FIG. 1, according to a non-limiting embodiment.

FIG. 10 illustrates a further example of the use case described above. Similarly to the illustrations of FIG. 7A, patient 104 is shown within imaging device 111, and optical scanner 312 is shown affixed inside the bore of imaging device 111 at a known position relative to frame of reference 200. Responsive to receiving a surface scan from scanner 312, computing device 300 is configured to retrieve an atlas image from memory 304 and to compare the point cloud data of the surface scan to the atlas image. For example, computing device 300 can be configured to receive input identifying a target tissue (e.g. the corpus callosum, illustrated at 1000 in FIG. 10), and to infer the position of the target tissue based on the surface scan and the atlas image (which may depict both external surface and internal anatomical structures). From the inferred position of the target tissue within patient 104, computing device 300 is configured to determine a transformation to apply to the parameters defining an imaging volume 1004 of imaging device 111, to center the imaging volume at a predefined angle on the target tissue.

Those skilled in the art will appreciate that n some embodiments, the functionality of processor 302 and application 316 may be implemented using pre-programmed hardware or firmware elements (e.g., application specific integrated circuits (ASICs), electrically erasable programmable read-only memories (EEPROMs), etc.), or other related components.

The scope of the claims should not be limited by the embodiments set forth in the above examples, but should be given the broadest interpretation consistent with the description as a whole.

The invention claimed is:

1. A method of maintaining patient registration in a surgical navigation system, comprising:
    obtaining, at a computing device, a position of a patient in a tracking system frame of reference, based on a fiducial marker array affixed in a first position relative to the patient;
    receiving, at the computing device, an initial surface scan depicting the patient and the fiducial marker array in the first position;
    prior to receiving an intraoperative image from a medical imaging device, receiving an intermediate surface scan depicting the patient;
    determining a further position of the patient in the tracking system frame of reference, based on a comparison of the intermediate surface scan and the initial surface scan, by:
        (i) registering the intermediate surface scan to the tracking system frame of reference,
        (ii) registering the initial surface scan to the intermediate surface scan,
        (iii) determining, based on the registration of the initial surface scan with the intermediate surface scan, a virtual position for the fiducial marker array, and
        (iv) based on the virtual position, determining the further position of the patient;
    obtaining a position of the medical imaging device in the tracking system frame of reference;
    selecting an imaging configuration based on a comparison of the further position and the position of the medical imaging device;
    controlling the medical imaging device to capture the intraoperative image according to the imaging configuration;
    responsive to capturing, by the medical imaging device, the intraoperative image depicting the patient:
        obtaining a position, in the tracking system frame of reference, of the fiducial marker array affixed in a second position relative to the patient;
        receiving a secondary surface scan depicting the patient and the fiducial marker array in the second position;
        detecting a deviation in a position of the fiducial marker array relative to the patient between the initial and secondary surface scans; and
        applying the deviation to the further position of the patient to generate an updated position of the patient in the tracking system frame of reference, based on the fiducial marker array affixed in the second position.

2. The method of claim 1, wherein detecting the deviation comprises:
    registering the initial and secondary surface scans to a common frame of reference based on the patient as depicted in each of the initial and secondary surface scans;
    determining the deviation by comparing the positions of the fiducial marker array as depicted in each of the initial and secondary surface scans.

3. The method of claim 1, wherein detecting the deviation comprises:
    identifying a set of anatomical features in the patient depictions of each of the preliminary and secondary surface scans;
    for each of the initial and secondary surface scans, determining a depicted position of the fiducial marker array relative to the set of anatomical features; and
    determining the deviation by comparing the depicted positions from the initial and secondary surface scans.

4. The method of claim 1, wherein receiving the initial surface scan and the secondary surface scan comprises receiving point cloud data from a handheld optical scanner.

5. The method of claim 1, further comprising receiving the intermediate surface scan as a point cloud data from an optical scanner mounted to the medical imaging device.

6. The method of claim 5, wherein registering the intermediate surface scan to the tracking system frame of reference comprises:
    retrieving a preconfigured position of the optical scanner relative to the medical imaging device from a memory; and
    registering the point cloud data to the tracking system frame of reference based on the position of the medical imaging device and the preconfigured position of the optical scanner.

7. A computing device for maintaining patient registration in a surgical navigation system, comprising:
    a communications interface connected to an optical scanner and a medical imaging device;
    a processor interconnected with the communications interface, the processor configured to:
        obtain a position of a patient in a tracking system frame of reference, based on a fiducial marker array affixed in a first position relative to the patient;
        receive an initial surface scan from the optical scanner, depicting the patient and the fiducial marker array in the first position;
        prior to receiving an intraoperative image from the medical imaging device, receive an intermediate surface scan depicting the patient;
        in order to determine a further position of the patient in the tracking system frame of reference, based on a comparison of the intermediate surface scan and the initial surface scan:
            (i) register the intermediate surface scan to the tracking system frame of reference,
            (ii) register the initial surface scan to the intermediate surface scan,
            (iii) determine, based on the registration of the initial surface scan with the intermediate surface scan, a virtual position for the fiducial marker array, and
            (iv) based on the virtual position, determine the further position of the patient;
        obtain a position of the medical imaging device in the tracking system frame of reference;
        select an imaging configuration based on a comparison of the further position and the position of the medical imaging device;

control the medical imaging device to capture the intraoperative image according to the imaging configuration;

responsive to capturing, by the medical imaging device, the intraoperative image depicting the patient:
   obtain a position, in the tracking system frame of reference, of the fiducial marker array affixed in a second position relative to the patient;
   receive a secondary surface scan depicting the patient and the fiducial marker array in the second position;
   detect a deviation in a position of the fiducial marker array relative to the patient between the initial and secondary surface scans; and
   apply the deviation to the further position of the patient to generate an updated position of the patient in the tracking system frame of reference, based on the fiducial marker array affixed in the second position.

8. The computing device of claim 7, the processor further configured to detect the deviation by:
registering the initial and secondary surface scans to a common frame of reference based on the patient as depicted in each of the initial and secondary surface scans;
determining the deviation by comparing the positions of the fiducial marker array as depicted in each of the initial and secondary surface scans.

9. The computing device of claim 7, the processor further configured to detect the deviation by:
identifying a set of anatomical features in the patient depictions of each of the preliminary and secondary surface scans;
for each of the initial and secondary surface scans, determining a depicted position of the fiducial marker array relative to the set of anatomical features; and
determining the deviation by comparing the depicted positions from the initial and secondary surface scans.

10. The computing device of claim 7, the processor further configured to receive the initial surface scan and the secondary surface scan as point cloud data from the optical scanner.

11. The computing device of claim 7, the processor further configured to receive the intermediate surface scan as point cloud data from the optical scanner.

12. The computing device of claim 11, the processor further configured to register the intermediate surface scan to the tracking system frame of reference by:
retrieving a preconfigured position of the optical scanner relative to the medical imaging device from a memory; and
registering the point cloud data to the tracking system frame of reference based on the position of the medical imaging device and the preconfigured position of the optical scanner.

13. A non-transitory computer-readable medium storing a plurality of instructions executable by a computing device for maintaining patient registration in a surgical navigation system, wherein execution of the instructions configures the computing device to:
obtain a position of a patient in a tracking system frame of reference, based on a fiducial marker array affixed in a first position relative to the patient;
receive an initial surface scan from the surface scanner, depicting the patient and the fiducial marker array in the first position;
prior to receiving an intraoperative image from a medical imaging device, receive an intermediate surface scan depicting the patient;
in order to determine a further position of the patient in the tracking system frame of reference, based on a comparison of the intermediate surface scan and the initial surface scan:
   (i) register the intermediate surface scan to the tracking system frame of reference,
   (ii) register the initial surface scan to the intermediate surface scan,
   (iii) determine, based on the registration of the initial surface scan with the intermediate surface scan, a virtual position for the fiducial marker array, and
   (iv) based on the virtual position, determine the further position of the patient;
obtain a position of the medical imaging device in the tracking system frame of reference;
select an imaging configuration based on a comparison of the further position and the position of the medical imaging device; and
control the medical imaging device to capture the intraoperative image according to the imaging configuration
responsive to capturing, from the medical imaging device, the intraoperative image depicting the patient:
   obtain a position, in the tracking system frame of reference, of the fiducial marker array affixed in a second position relative to the patient;
   receive a secondary surface scan depicting the patient and the fiducial marker array in the second position;
   detect a deviation in a position of the fiducial marker array relative to the patient between the initial and secondary surface scans; and
   apply the deviation to the further position of the patient to generate an updated position of the patient in the tracking system frame of reference, based on the fiducial marker array affixed in the second position.

* * * * *